United States Patent [19]

Kashiwagi et al.

[11] Patent Number: 5,567,443
[45] Date of Patent: Oct. 22, 1996

[54] METHOD OF TREATING INFLAMMATORY DISEASES

[75] Inventors: Nobuhito Kashiwagi; Syojiroh Asakura; Tatsuo Ide, all of Takasaki; Masato Sakurai, Naganohara-machi; Masakazu Adachi, Takasaki; Katsumi Tomiyoshi, FuJimi-mura; Tsuneo Hirano, Maebashi, all of Japan

[73] Assignees: Japan Immunoresearch Laboratories Co., Ltd., Gunma; Sekisui Chemical Co., Ltd., Osaka, both of Japan

[21] Appl. No.: 262,519

[22] Filed: Jun. 20, 1994

[30] Foreign Application Priority Data

Aug. 4, 1993 [JP] Japan .................................. 5-193481

[51] Int. Cl.⁶ .................................. B29C 49/00
[52] U.S. Cl. .................................. 424/529
[58] Field of Search .................................. 424/529

[56] References Cited

FOREIGN PATENT DOCUMENTS 91118439  10/1991  European Pat. Off. .

OTHER PUBLICATIONS

Medline 91–111849 1990.
Medline 91–353062 1991.
Medline 92–139659 1991 (Nov.)
Medline 86–247880 (May) 1986.
14th Conference of The Japanese Inflammation Society Program & Preliminary Report (Jun. 24 and 25, 1993).

*Primary Examiner*—Paul J. Killos
*Attorney, Agent, or Firm*—Sughrue, Mion, Zinn, Macpeak & Seas

[57] ABSTRACT

A method of treating inflammatory diseases, in which peripheral blood of a patient suffering from an inflammatory disease is made into contact with a carrier whose affinity for inflammation-associated cells is higher than that for lymphocytes, and the thus-obtained treated blood is returned to the patient.

According to the present invention, inflammatory diseases can be promptly treated without causing adverse side effects to patients, because drug therapy is not needed.

6 Claims, 2 Drawing Sheets

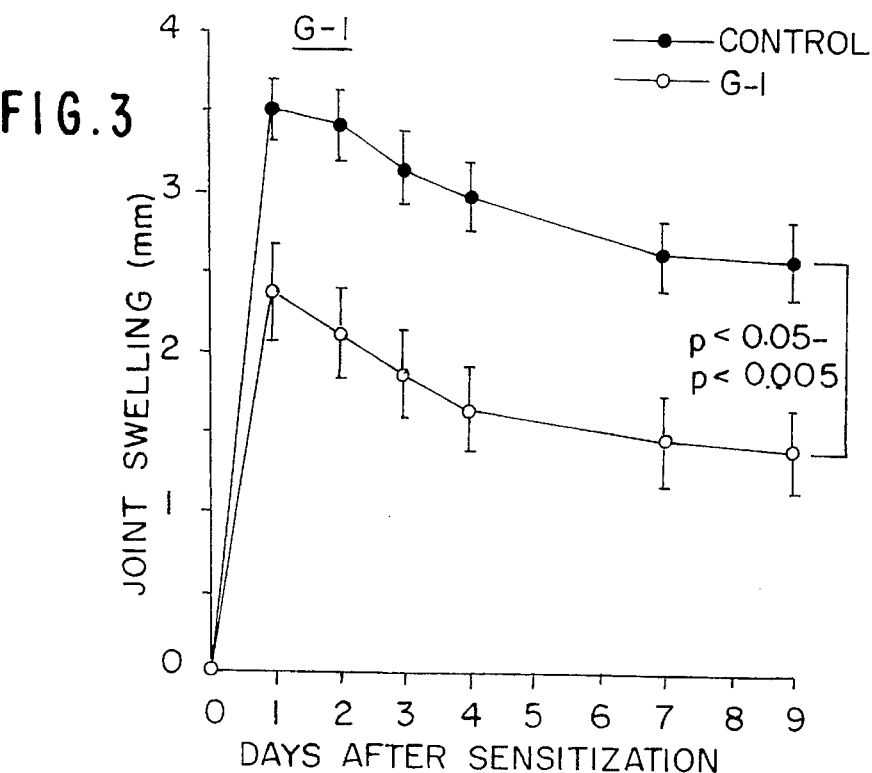
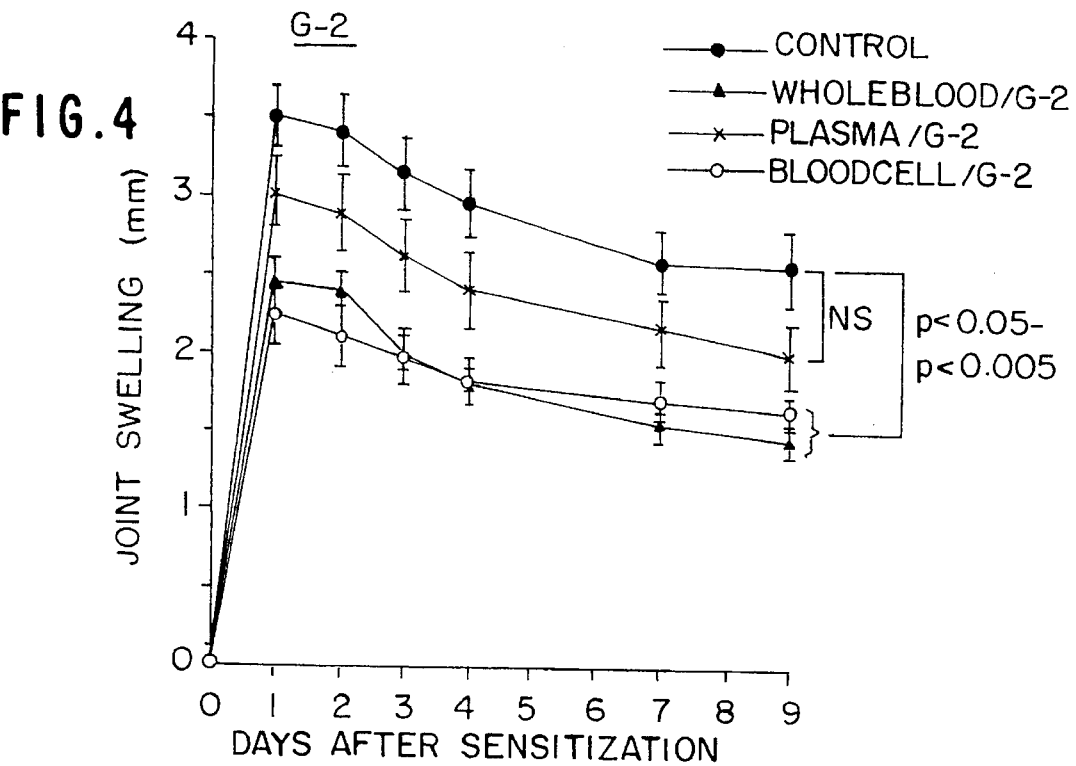

METHOD OF TREATING INFLAMMATORY DISEASES

BACKGROUND OF THE INVENTION

1. Field of the Invention

The present invention relates to a method of treating inflammatory diseases, and more particularly, to a method of treating inflammatory diseases wherein the peripheral blood of a patient suffering from an inflammatory disease is treated to remove granulocytes therefrom and then the thus-treated blood is returned to the patient for alleviating or curing the symptoms of various inflammatory diseases.

2. Description of Related Art

Phagocytes such as neutrophilic leukocytes gather in inflamed tissues, and form a cell mass having various functions such as phagocytosis, production of activated oxygen, release of granular enzymes, migration into tissues, adhesion to tissues, etc. They play a very important role in the defense mechanism of a living body against invading microorganisms.

It is known that when such a cell mass locally infiltrates excessively or chronically, significant disorders are caused in the tissue. For example, it has been reported that phagocytes, in particular neutrophilic leukocytes, play an important role in the onset mechanism of reflow disorders after ischemia of myocardial infarct, etc. (J. L. Romson, et al., Circulation, 67, 1016–1023, 1983), pulmonary edema induced by sepsis, etc., called ARDS (adult respiratory distress syndrome) (J. E. Powe, et al., Crit. care. Med., 10 712–718, 1982), multiple organ failure (E. A. Deitch, Ann. Surg., 216, 117–134, 1992), rheumatoid arthritis having a background of biological reaction and immunologic reaction (P. R. Elford, P. H. Coper, Arthritis Rheum. 34, 325–332, 1991; D. Schrier et al., Am. J. Pathol., 117, 26–29, 1984) and glumerulonephritis (L. Baud et al., Kidney Int., 20, 332–339, 1981).

In addition, although the onset of ARDS, a clinical syndrome of pulmonary edema caused as a result of tissue disorders of the lung, has many causes such as respiratory infections, physicochemical injuries given to the lung, sepsis, poisoning by drugs, and serious traumas, the histological findings of ARDS are common. That is, general pulmonary alveolus disorders, angiectasia, disorders in epithelial cells and the resultant edema formation, and accumulation of neutrophilic leukocytes are commonly found. Therefore, it is considered that neutrophilic leukocytes profoundly participate in the inflammatory reaction in ARDS (A. A. Fowler, et al., Am. Rev. Respir., 136, 1225–1231, 1987). In fact, functions of neutrophilic leukocytes in peripheral blood of a patient suffering from sepsis (S. D. Tennenburg, et al., Arch. Surg., 123, 171–175, 1988) and those in pulmonary exudates of ARDS have been found altered (T. R. Martin, et al., Am. Rev. Respir. Dis., 144, 252–262, 1991). Also, it is reported that a migration stimulation factor IL-8 (C. E. Hack, et al., Infect. Immun., 60, 2842–2852, 1992), a factor TNF which participates the activation of IL-8, (T. M. Hyers., et al., Am. Rev. Respir. Dis., 144, 268–271, 1991), and endotoxin (P. E. Parsons, et al., Am. Rev. Respir. Dis., 140, 294–301, 1989) all elevate in the patient's blood.

Accordingly, in order to treat these diseases by controlling the actions and functions of neutrophilic leukocytes, various approaches have been taken, which include: administration of N-acetylcysteine (NAC), which is an SOD against the production of activated oxygen (G. R. Bernard, et al., J. Clin. Invest., 73, 1772–1784, 1984); administration of a granulocyte elastase inhibitor (M. Ogawa, et al., Res. Comm. Chem. Path. Pharm., 55, 271–274, 1987); administration of an anti-endotoxin antibody (A. P. Wheeler, et al., Am. Rev. Respir. Dis., 142, 775–781, 1990); and application of an anti-adhesion molecular monoclonal antibody such as CD18 in an attempt to inhibit adhesion of neutrophilic leukocytes to the tissue (N. B. Vedder, et al., J. Clin. Invest., 81, 939–944, 1988).

However, any of these approaches for the treatment of inflammatory diseases cannot avoid causing adverse side effects because the substance administered to the patient is foreign to his or her body.

In view of the foregoing, the present invention is to provide a method of treating inflammatory diseases by not administering any drugs but by controlling the content of an in vivo component which participates in the onset of inflammatory diseases.

The present inventors have conducted careful studies mainly focusing on the relation between inflammatory diseases and the quantity of the inflammation-associated cells such as granulocytes and monocytes, and the relation between the concentration of these cells in blood in inflammatory diseases and the concentration of inflamed tissue, and as a result, they have found that when inflammation-associated cells are selectively removed from the peripheral blood of a patient suffering from an inflammatory disease and then the thus-treated blood is returned to the patient, the inflammatory disease is alleviated and healing of the disease is accelerated. The present invention was accomplished based on this finding.

SUMMARY OF THE INVENTION

Accordingly, an object of the present invention is to provide a method of treating inflammatory diseases which comprises contacting peripheral blood of a patient suffering from an inflammatory disease with a carrier whose affinity for inflammation-associated cells is higher than that for lymphocytes, and returning the thus-obtained treated blood to the patient.

The above and other objects, features and advantages of the present invention will become apparent from the following description.

Figure 2:
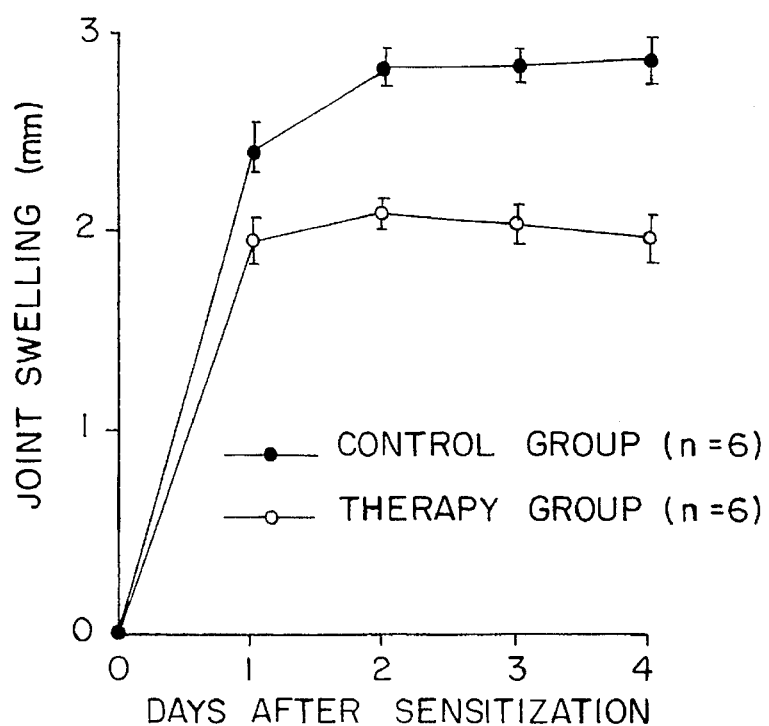

Each of the symbols in the attached FIG. 1 denotes the portion as follows:

1: Inflammation-associated cell adsorbing section
2: Arterial blood port
3: Venous blood port
4: Absorbant
5: Blood pump
6: Drug injection port
7: Blood warmer
8: Arterial pressure meter
9: Venous pressure meter
10: Drug injection port FIG. 2 is a graph showing the effect of G-1 therapy according to the present invention performed on rabbit arthritis.

FIG. 3 is a graph showing the effect of G-1 therapy according to the present invention performed on rabbit arthritis.

FIG. 4 is a graph showing the effect of G-2 therapy according to the present invention performed on rabbit arthritis.

DETAILED DESCRIPTION OF THE INVENTION AND PREFERRED EMBODIMENTS

The inflammatory diseases to which the method of the present invention is suitably applied include ARDS, multiple organ failure (MOF), allergic diseases, rheumatoid arthritis, autoimmune diseases, and reflow disorders occurred after ischemia of myocardial infarct, in all of which a factor produced by granulocytes is responsible. Of these diseases, ones that are considered to be very difficult to treat successfully, namely, ARDS and rheumatoid arthritis are especially suitable target diseases. In arthritis, in particular, treatment by drugs such as nonsteroidal anti-inflammatory drugs or DMARDS sometimes ends up with no effects, and patients are difficult to be controlled.

In this specification, the inflammation-associated cells encompass the cells which are present in blood and which affect the onset mechanism of inflammation and aggravation thereof. Specific examples of such cells include CD11b positive cells, namely, granulocytes (CD15 positive cells) and monocytes (CD14 positive cells).

No particular limitation is imposed on the materials of the carrier having an affinity for granulocytes higher than that for lymphocytes (hereinafter such specific carriers are simply referred to as "carrier"), as long as they meet this affinity requirement and are not harmful to blood with which they contact. Naturally, carriers that are capable of selectively adsorbing CD11b positive cells are most preferred. Examples of materials suitable as such carriers include materials having a contact angle with water between 55° to 95°. Specifically polystyrene, cellulose acetate, 6-Nylon, 11-Nylon, and polyethylene terephthlate are mentioned.

In this specification, the contact angle is defined to be an angle which is made between a solid surface and a free surface of a stationary liquid at the point of contact therebetween, and is measured in the liquid.

The size and the shape of the carrier are arbitrarily determined. However, it is preferred that the size be large enough for being distinguished over blood cells, and the shape be such that the contacting face with blood is maximized. In other words, such shape that can achieve an effective contact is preferred. For example, beads having a diameter of 0.1 to 10 mm may be used.

In the present invention, peripheral blood of a patient suffering from an inflammatory disease is made into contact with the carrier. During treatment, inflammation-associated cells are adsorbed onto the carrier surface. The treated blood from which inflammation-associated cells are removed are returned to the patient body as a blood cell component. Thus, desired results are obtained, and there is no need to further remove plasma constituents from the treated blood. To the treated blood, any blood constituents may be arbitrarily augmented as desired.

No particular limitation is imposed on means for effecting the above-described treatment as long as inflammation-associated cells are effectively adsorbed onto the carrier surface, and the treated blood can be recovered in such a manner that can be returned to the patient. Also, means for returning the treated blood to the patient is not particularly restricted. For example, blood may be exogenously circulated in a continuous manner or with a batch system to remove inflammation-associated cells, and then the treated blood may be intravenously administered according to a method known per se.

The exogenous circulation is continuously performed by the use of an inflammation-associated cell removing apparatus equipped with an inflammation-associated cell adsorbing section which is filled with carriers, an inlet section for introducing blood into the adsorbing section, and an outlet section for discharging the blood outside the adsorbing section. A specific example of this apparatus is described in EPO319961-A2 as a granulocyte removing apparatus.

The inflammation-associated cell removing apparatus useful in the practice of the invention will now be explained referring to FIG. 1.

Figure 1:
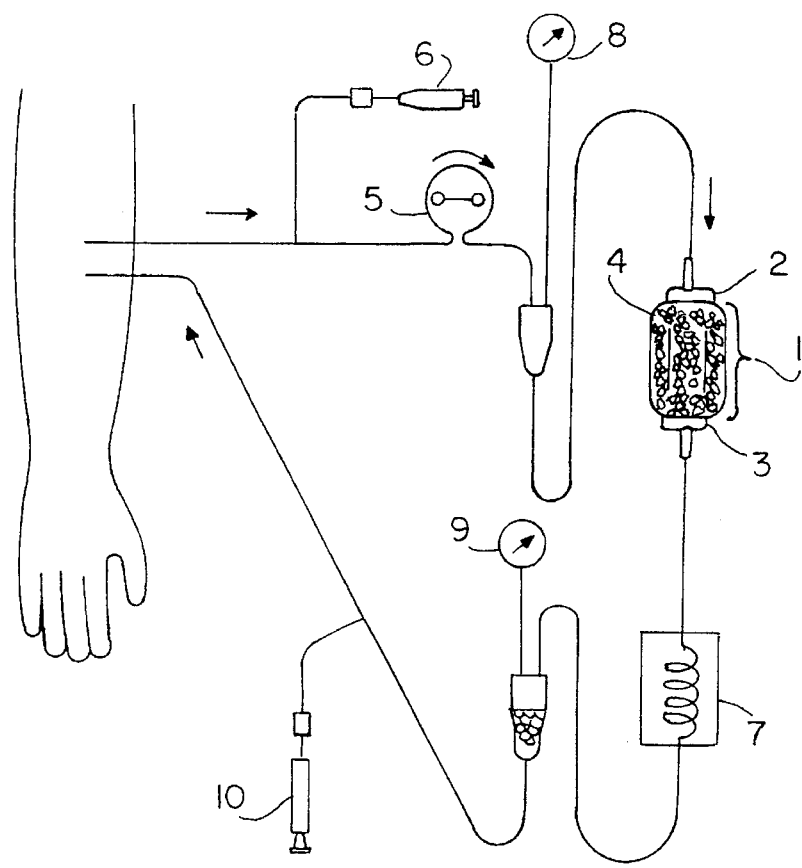
FIG. 1 is a scheme showing an apparatus for removing inflammation-associated cells used in the practice of the present invention.

In FIG. 1, numeral 1 denotes an inflammation-associated cell adsorbing section, where absorbant 4 having a higher affinity for inflammation-associated cells than for lymphocytes are charged.

At one end of the adsorbing section 1, arterial blood port 2 for introducing the blood to be treated (blood of a patient who suffers from an inflammatory disease) into the adsorbing section is provided. At the other end, there is provided venouse blood port 3 for discharging the treated blood which does no more contain inflammation-associated cells as a result of contacting the blood with the surface of the carriers.

This apparatus can continuously remove inflammation-associated cells when blood is exogenously circulated as in general plasma exchange therapy. The apparatus may further be provided with piping 11 (not shown in FIG. 1) and blood pump 5 which are made of, for example, non-toxic materials such as silicone rubbers or polyvinyl chloride which are generally used as transportation materials.

On the circulation line of the blood discharged from the outlet section, may be provided an arterial pressure meter 8 and venous pressure meter 9, drug injection port 6 for dosing drugs for inhibiting clotting of blood, such as heparin, and another drug injection port 10 for dosing drugs for inhibiting the action of the anticoagulant, such as protamine, and blood warmer 7 for elevating the blood temperature which tends to drop during the exogenous circulation. Furthermore, an ordinary detector for detecting a blood profile of the circulating blood and a blood constituent augmenter for augmenting insufficient blood constituents other than inflammation-associated cells may be included.

As the blood constituents for augmentation, constituent transfusion may be utilized.

When the peripheral blood of a patient suffering from an inflammatory disease is circulated in the above-described inflammation-associated cell removing apparatus for 1 hour, about 30% of leukocytes which are mainly composed of granulocytes are adsorbed onto the surface of the carrier in the apparatus. During this operation, the concentration of granulocytes, especially that of neutrophilic leukocytes does not drastically go down. A possible reasoning is as follows: Granulocytes, especially neutrophilic leukocytes flock in the inflamed tissue and adhere to and infiltrate into the tissue. This fact is considered to be a cause of disorders in tissue and aggravated inflammation via the production of various inflammation-provoking substances at the local tissue and activated oxygen. Accordingly, when granulocytes are removed from the circulatory blood, in vivo homeostasis functions to mobilize granulocytes from the marginal pool so that the count of granulocytes in blood is kept constant.

Consequently, the count of granulocytes infiltrating into the local inflamed tissue drops to promote healing of the patient from inflammation, but the count of granulocytes in the peripheral blood does not go down immediately.

The manner of the treatment according to the present invention by way of the exogenous circulation may vary depending on the conditions of patients. Generally speaking, blood is circulated for 30 minutes to 90 hours per one treatment with the blood flow of 30 ml/min. Of course, the amount of the carrier used and its adsorption characteristics affect these conditions. For example, in the clinical example which will be described later, a one-hour blood circulation per treatment with a blood flow of 30 ml/min was performed 1 to 3 times a week for 1 to 8 weeks. This treatment exhibited good results on rheumatoid arthritis.

In the case where the blood treated by way of a batch system is intravenously administered to the patient, substantially the same process as the above-described exogenous circulation may be followed. The quantity of blood to be collected/administered is generally from 150 to 450 ml/day.

By the method of the present invention, symptoms of inflammatory diseases are alleviated and healing from disease is accelerated. In the practice of the invention, it is also possible to perform a concurrent therapy to obtain a more prompt treatment effect, in which a drug therapy using anti-inflammatory drugs, antimicrobial drugs, antiviral drugs, etc. may be effected together with the present treatment. In the case where such concurrent therapy is performed, less dose of drug than the dose under a single drug therapy suffices. Accordingly, the concurrent therapy is advantageous in that adverse side effects can be reduced compared to the case of a single drug therapy.

With the method according to the present invention, inflammatory diseases can be promptly alleviated and cured without causing adverse side effects to patients.

EXAMPLES

The present invention will further be described by way of examples, which should not be construed as limiting the invention thereto. In the following Examples, the counts of leukocytes such as granulocytes and monocytes were obtained by the use of an automatic analyzer (THMS H1, Technicon).

Example 1

Cellulose acetate beads (11 g) were packed in a column having an inner diameter of 1.5 cm and a length of 5 cm (Bio-Rad, Richmond, Calif.). The packed column was steam-sterilized under pressure. This serves as an inflammation-associated cell-free column (may be referred to as a "G-1 column", inflammation-associated cell adsorbing section in FIG. 1).

The ear vein of rabbit was used in the test. A circuit as shown in FIG. 1 was provided, and an exogenous circulation of blood was performed with a flow rate of 2 ml/min for 1 hour. CD11b positive cell removing efficiency was investigated.

Specifically, 4 rabbits were provided for the test, and blood of each rabbit was circulated for 1 hour at a flow rate of 2 ml/min. Subsequently, beads were taken out of the column, and the leukocytes adhered onto the surface of the beads were recovered using phosphate buffer (PBS) containing EDTA, and the recovered leukocytes were analyzed. The count of peripheral leukocytes before undergoing treatment with the G-1 column and its blood profile were obtained by the use of an apparatus THMS H1 manufactured by Technicon. Assuming that the whole blood quantity of a rabbit is 5% of its body weight, the number of the total granulocytes in blood is calculated to be $(3.02+/-1.60) \times 10^8$. Meanwhile, the number of leukocytes recovered from the beads by the use of EDTA-PBS was found to be $(5.2+/-1.3) \times 10^7$. When the eluate was analyzed by flow cytometry, the proportion of CD11b positive cells which are the marker for granulocytes and monocytes was 76.2+/-6.0%. The count of the CD11b positive cells was $(4.2+/-1.4) \times 10^7$. This was taken as the count of the recovered granulocytes, and was divided by the count of the total number of granulocytes. As a result, the rate of recovery into the G-1 column was calculated to be 13.7+/-1.9%. Based on the histogram of flow cytometry performed on the eluate from G-1 beads and peripheral blood of one of the test rabbits, distribution of CD11b positive cells was investigated. As a result, it was found that general T-cell markers CD5 positive cells and CD11b positive cells both existed about 30% in the peripheral blood, whereas in the beads eluate of G-1 column, the proportions of CD5 positive cells and CD11b positive cells were 7.1% and 76.0%, respectively. From this, the recovery rate of CD11b positive cells was about 10 fold of that of CD5 positive cells. Because CD11b positive cells are phagocytes, and CD5 positive cells are T-cells, it was found that G-1 column selectively adsorbs phagocytes which serve as a more important inflammation aggravating factor than T-cells.

Example 2

Endotoxin (LPS) (2 mg/kg) was administered to a rabbit from the ear vein and a pulmonary edema model was established.

Japanese white rabbits (female, 15–16 weeks old) were used in groups. Eight rabbits in a control group were given only LPS. The remainder 8 rabbits in a test group were given LPS, and immediately thereafter, they were treated as described in Example 1 (exogenous blood circulation, referred to as a G-1 therapy) for 1 hour. The G-1 therapy was performed under the same conditions for the successive two days. In other words, the rabbits in the test group were treated with G-1 therapy for 3 times in total.

As a result, 5 out of 8 rabbits in the control group died within 48 hours. By contrast, only one died in the G-1 therapy group. It is thus clear that G-1 therapy is effective against pulmonary edema.

During the test, the counts of neutrophilic leukocytes dropped when counted 1 hour after LPS administration, counted in the control group, or counted in the G-1 therapy group. The % reduction of neutrophilic leukocytes in the control group and in the G-1 therapy group were 91.9+/-1.7 and 74.0+/-7.2, respectively, thus the % reduction of neutrophilic leukocytes from the peripheral blood was smaller. Simultaneously, the beta-glucuronidase activity was compared between the control group and the G-1 therapy group. As a result, no difference was found.

Example 3

An emulsion obtained by mixing 4 mg of eggwhite albumin (OVA) and 1 ml of complete Freund's adjuvant was subcutaneously given to an rabbit and sensitized. Two weeks thereafter, OVA sensitization was repeated in the same manner. After 5 days has passed from the last sensitization, physiological saline (1 ml) containing OVA (5 mg) was injected at the knee joint to cause arthritis.

When 10 minutes, 1 day, 2 days and 4 days have elapsed, G-1 therapies were performed using the rabbit ear vein and a circuit as shown in FIG. 1 at a flow rate of 2 ml/min for 1 hour/treatment. It was revealed that G-1 therapy significantly inhibited the swelling in joint (FIG. 2).

About 90% of CD11b positive cells were present in the joint fluid of the diseased region. After G-1 therapy, it was found that about 90% of the leukocytes recovered from the column in inflammation associated cell-adsorbing section was CD11b positive cells. This demonstrates that the G-1 therapy was effective in removing CD11b positive cells from the blood.

OVA was injected into the joint of each rabbit. One day after the onset of arthritis, the cells in the joint fluid of the diseased region were counted. The same test was performed on two groups (control and G-1 therapy groups), and the results were compared. As the Table 1 data show, the number of CD11b positive cells was smaller than that in the control group. In particular, significant decrease was found in the count of monocytes with a level of significance of not more than 0.1%.

TABLE 1

| | Counts of leukocytes in joint fluid of diseased region ($\times 10^7$) | | | |
|---|---|---|---|---|
| | | CD11b positive cells | | |
| Group | Leukocytes | Granulo-cytes | Mono-cytes | CD5 positive cells |
| Control | 2.56+/−0.60 | 2.12+/−0.56 | 0.33+/0.04 | 0.03+/−0.01 |
| G-1 Therapy | 1.33+/−0.25 | 1.13+/−0.22 | 0.13+/0.02 | 0.01+/−0.01 |

(Mean+/−S.E., n=7)

Example 4

Blood (10 ml) collected from a rabbit with heparin was incubated with cellulose acetate beads (11 g) which were autoclave-treated in a syringe having a capacity of 20 ml (Terumo Co.) (37° C., 1 rpm, 1 hour). The thus-treated blood was intravenously injected to the arthritis-induced rabbit according to Example 3. Swelling of the joint was measured during passage of time to check the effect (G-2 therapy).

The test was performed using the following groups of rabbits, each group consisting of 5 rabbits:

Control: Arthritis was induced, but not treated at all.

G-1: 10 minutes after arthritis was induced, G-1 therapy of Example 3 was performed for 1 hour.

Whole blood/G-2: 10 minutes after arthritis was induced, treated blood according to the above-description was intravenously injected.

Plasma/G-2: Plasma separated (2500 rpm, 10 min., room temp.) and recovered from the above-mentioned treated blood was passed through 0.2 micron milipoa filter, and the filtered plasma was intravenously injected 10 minutes after arthritis was induced.

Blood cell/G-2: Blood cells separated from the above-mentioned treated blood (2500 rpm, 10 min., room temp.) were suspended in physiological saline and centrifugally separated (2500 rpm, 10 min., room temp.), followed by removing the supernatant and resuspending in physiological saline. The obtained was intravenously injected 10 minutes after arthritis was induced.

The results are shown in FIGS. 3 and 4.

G-1 group showed significant alleviation of joint swelling over control group for the full term of observation. For example, at day 4, G-1 group inhibited 45.4% of swelling as compared to control (Control Group: 3.00 mm, G-1 Group: 1.64 mm) (FIG. 3).

In G-2 therapy, Plasma/G-2 group did not show significant alleviation in joint swelling compared to the control group. Whole blood/G-2 group and Blood cell/G-2 group exhibited a roughly equivalent effect (FIG. 4).

From these results, it is understood that the blood constituents of the treated blood have an anti-inflammatory effect.

Example 5 (Clinical test)

63 patients who have been diagnosed to have RA (rheumatoid arthritis) according to the diagnosis standards by American Rheumatoid Association (ARA) and already suffering from RA for over 6 months were treated with the apparatus as shown in FIG. 1 (hereinafter simply referred to as G-1) in such a manner that his or her venous blood was exogenously circulated with a flow rate of 30 ml/min. for 1 hour in each treatment. The blood circulating treatment was performed 1 to 3 times a week for 1 to 8 weeks. The results are shown below.

(1) Adsorption characteristics of G-1

In six cases among the cases treated by the exogenous granulocyte adsorption therapy, blood was collected before and after passing G-1 during the period they were treated, and the profiles of leukocytes and serum proteins before and after passing G-1 were examined. As a result, blood constituents which were adsorbed were exclusively granulocytes and monocytes. There were no significant differences between the "before" and "after" counts of red cells, lymphocytes, platelets, total protein, albumin, IgG, IgA, IgM and RF.

On the seven patients treated by the exogenous granulocyte adsorption therapy, leukocytes were recovered from G-1 immediately after the treatment, and the proportion of granulocytes in the leukocytes adsorbed onto G-1 was studied. As a result, 95% of the leukocytes adsorbed onto G-1 were granulocytes (including monocytes CD15 positive cells). This shows that G-1 is highly specific to granulocytes.

(2) Adsorption efficiency of granulocytes

In order to investigate the adsorption efficiency of G-1 to granulocytes and lymphocytes, the numbers of granulocytes and lymphocytes in peripheral blood were counted at the inlet portion and outlet portion of G-1 in all the 63 cases. Concerning granulocytes, larger the number of granulocytes in peripheral blood is, larger the number of those adhered to G-1. Namely, the granulocyte counts in peripheral blood and the counts of granulocytes adhered to G-1 are in a positive correlation (p=0.0001). By contrast, lymphocytes were scarcely adhered to G-1, and there was no correlation between the counts of peripheral blood lymphocytes and adhered lymphocytes. The numbers of granulocytes and lymphocytes adhered to G-1 were $4.91+/-0.26\times 10^9$ and $0.12+/-0.03\times 10^9$, respectively. The adsorption efficiency of G-1 for granulocytes and lymphocytes were 48.3+/−1.21 (%) and 5.4+/−1.04 (%), respectively.

(3) Evaluation of effectiveness

The Lansbury index is an evaluation item for monitoring effectiveness against RA. It was improved by 21.1% (60.2% to 47.5%) after G-1 therapy as compared to the value before the therapy (p<0.001).

Factors affecting the Lansbury index (The American Journal of Medicine, Vo. 81, No. 4, P565–578 (1986)) were studied. As a result, all the factors excepting ESR (erythrocyte sedimentation rate) were significantly improved in all the treated cases. In particular, points of tender joints, swelling joints and active joints were significantly lowered after G-1. Concerning the points of tender joints, reduction was observed in 100% of the effective cases. 16 cases among all the 59 cases revealed elimination of the points of algesic joints. ESR was not effectively improved, but showed an inclination of reduction.

The clinical results in Example 5 have been sent to Nippon Ensho Gakkai (Japan Inflammation Association). The content of the article contributed to the Association (Japanese Journal of Inflammation, Vol. 14, No. 3, 1994) is incorporated herein by reference. In addition, the disclosures of Japanese Patent Application No. 193481/1993 and the 14th annual meeting of the Japan Inflammation Association dated Jun. 24 and 25, 1993 (the program of this meeting has been printed on Jun. 20, 1993) are incorporated herein by reference, too.

We claim:

1. A method of treating inflammatory diseases which comprises contacting peripheral blood of a patient suffering from an inflammatory disease with a carrier whose affinity for inflammation-associated cells is higher than that for lymphocytes so as to remove said cells from the blood, and returning the thus treated blood to the patient.

2. The method according to claim 1, wherein blood of the patient is continuously passed through an inflammation-associated cell removing apparatus equipped with an inflammation-associated cell adsorbing section which accommodates the carrier as described in claim 1, an inlet section for introducing the blood into the adsorbing section, and an outlet section for discharging the blood outside the adsorbing section, before returning to the patient.

3. The method according to claim 1, wherein the treated blood is returned to the patient in the form of cell constituents.

4. The method according to claim 1, wherein the inflammatory disease is rheumatoid arthritis.

5. The method according to claim 1, wherein the inflammation-associated cells comprise granulocytes and monocytes.

6. The method according to claim 1, wherein the inflammation-associated cells comprise CD11b positive cells.

* * * * *